US010335118B2

(12) United States Patent
Kanayama et al.

(10) Patent No.: US 10,335,118 B2
(45) Date of Patent: Jul. 2, 2019

(54) ULTRASONIC DIAGNOSTIC APPARATUS, MEDICAL IMAGE PROCESSING APPARATUS, AND MEDICAL IMAGE PARALLEL DISPLAY METHOD

(71) Applicants: Yuko Kanayama, Nasushiobara (JP); Naohisa Kamiyama, Utsunomiya (JP)

(72) Inventors: Yuko Kanayama, Nasushiobara (JP); Naohisa Kamiyama, Utsunomiya (JP)

(73) Assignee: Canon Medical Systems Corporation, Otawara-shi (JP)

(*) Notice: Subject to any disclaimer, the term of this patent is extended or adjusted under 35 U.S.C. 154(b) by 349 days.

(21) Appl. No.: 13/713,452

(22) Filed: Dec. 13, 2012

(65) Prior Publication Data
US 2013/0184582 A1 Jul. 18, 2013

(30) Foreign Application Priority Data

Jan. 16, 2012 (JP) ................................. 2012-006038

(51) Int. Cl.
A61B 8/00 (2006.01)
A61B 8/14 (2006.01)

(52) U.S. Cl.
CPC .............. A61B 8/463 (2013.01); A61B 8/145 (2013.01); A61B 8/4254 (2013.01); A61B 8/4444 (2013.01); A61B 8/4488 (2013.01)

(58) Field of Classification Search
CPC ........ A61B 8/463; A61B 8/5269; A61B 8/488
(Continued)

(56) References Cited

U.S. PATENT DOCUMENTS 5,645,066 A * 7/1997 Gandini ................. B82Y 15/00
128/916
6,102,859 A * 8/2000 Mo ............................... 600/443
(Continued)

FOREIGN PATENT DOCUMENTS

CN 101396288 A 4/2009
CN 101409763 A 4/2009
(Continued)

OTHER PUBLICATIONS

Kumar, "How do I get an optimal image?", May-Aug. 2009, Annals of Cardiac Anaesthesia, vol. 12, No. 2, pp. 173.*
(Continued)

Primary Examiner — Carolyn A Pehlke
Assistant Examiner — Marjan Saboktakin
(74) Attorney, Agent, or Firm — Oblon, McClelland, Maier & Neustadt, L.L.P.

(57) ABSTRACT

According to one embodiment, an ultrasonic diagnostic apparatus includes an ultrasonic probe, scanning unit, ultrasonic image data generation unit, layout setting unit, and display unit. The ultrasonic probe includes transducers. The scanning unit scans an object with an ultrasonic beam via the ultrasonic probe. The ultrasonic image data generation unit generates data of ultrasonic images based on outputs from the scanning unit. The layout setting unit sets a specific display layout based on an aspect ratio of a display frame of the ultrasonic image or a size of the ultrasonic image and the number of ultrasonic images for simultaneous display. The display unit displays the ultrasonic images in accordance with the set display layout.

15 Claims, 9 Drawing Sheets

(58) Field of Classification Search
USPC .......................................................... 600/440
See application file for complete search history.

(56) References Cited

U.S. PATENT DOCUMENTS

| | | | |
|---|---|---|---|
| 6,704,440 B1* | 3/2004 | Kump | 382/132 |
| 2004/0015079 A1* | 1/2004 | Berger | A61B 8/461 |
| | | | 600/437 |
| 2006/0013462 A1* | 1/2006 | Sadikali | 382/132 |
| 2007/0120763 A1* | 5/2007 | De Paepe et al. | 345/1.3 |
| 2009/0082675 A1* | 3/2009 | Gunji | A61B 8/0883 |
| | | | 600/459 |
| 2010/0106017 A1 | 4/2010 | Shin et al. | |

FOREIGN PATENT DOCUMENTS

| | | |
|---|---|---|
| CN | 102090902 A | 6/2011 |
| JP | 11-127343 A | 5/1999 |
| JP | 2008-509456 A | 3/2008 |
| JP | 2008-253549 A | 10/2008 |
| JP | 2009-240829 A | 10/2009 |
| WO | WO 2005/053539 A1 | 6/2005 |

OTHER PUBLICATIONS

HD11 XE Ultrasound System Quick Guide, Phillips Medical Systems, Nov. 2006.*
Combined Office Action and Search Report dated Apr. 29, 2014, in Chinese Patent Application No. 201210486990.5 with English translation.
Office Action dated Oct. 20, 2015 in Japanese Patent Application No. 2012-006038.

* cited by examiner

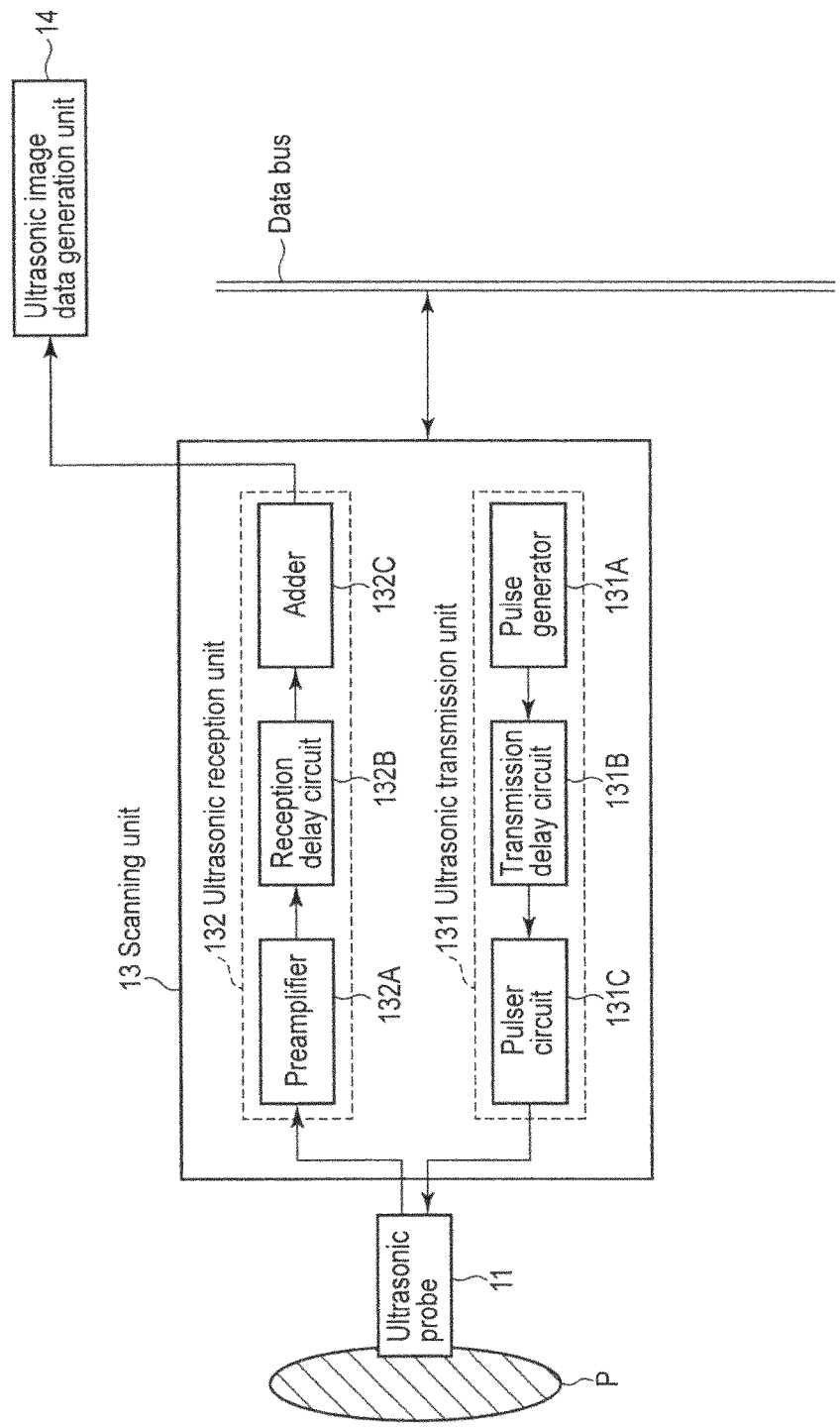
F I G. 2

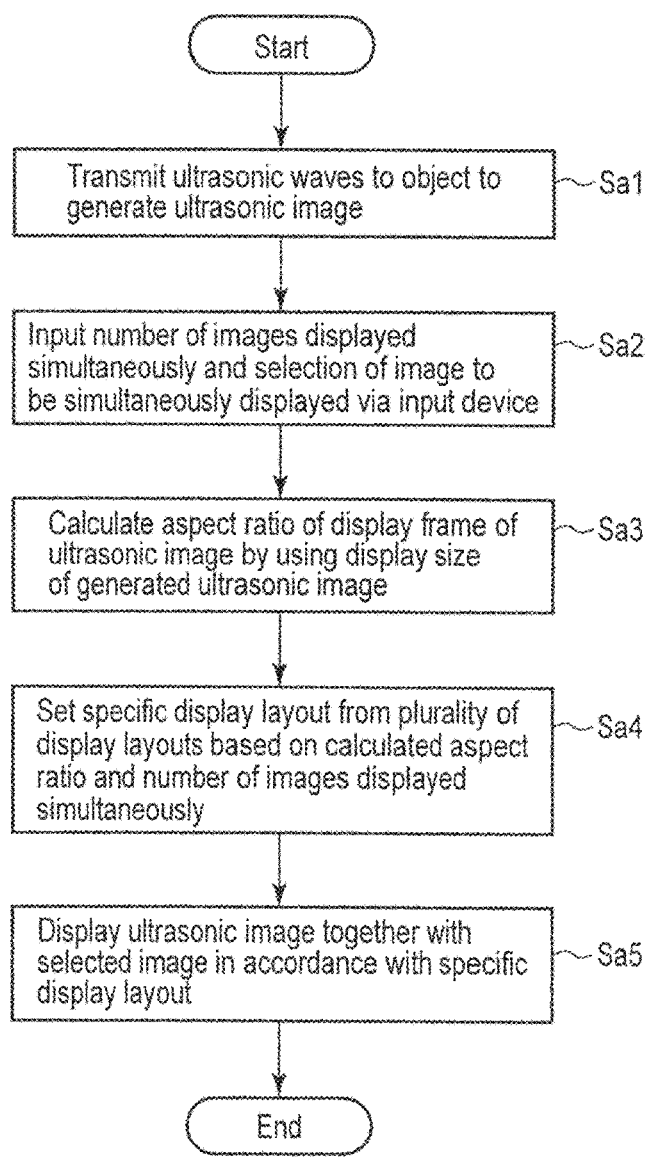
F I G. 4

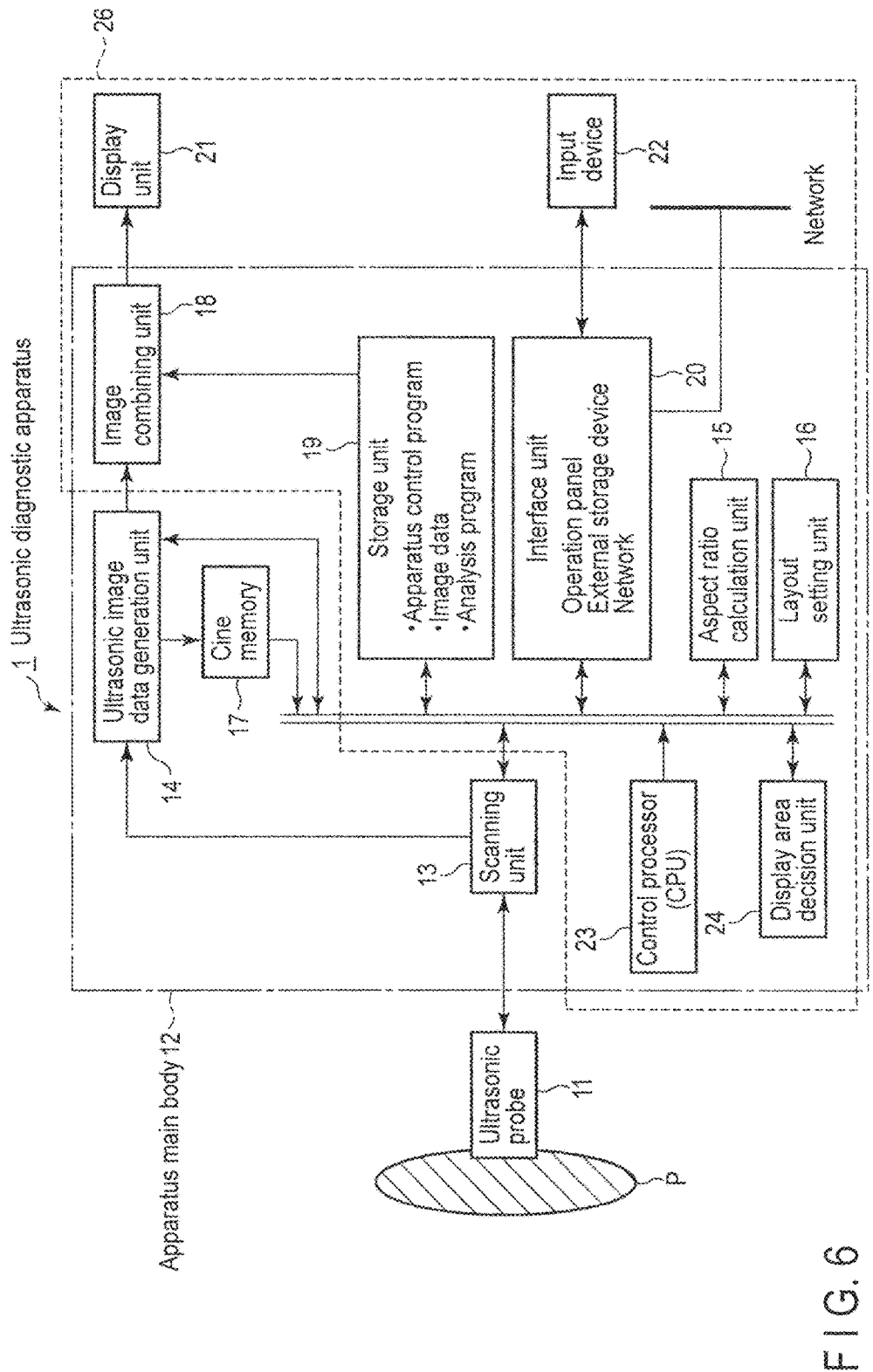
F I G. 6

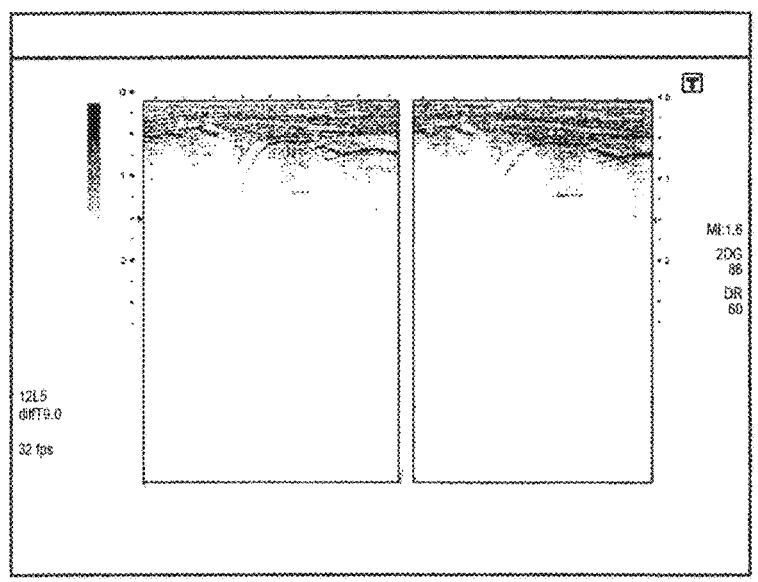
F I G. 10

ULTRASONIC DIAGNOSTIC APPARATUS, MEDICAL IMAGE PROCESSING APPARATUS, AND MEDICAL IMAGE PARALLEL DISPLAY METHOD

CROSS-REFERENCE TO RELATED APPLICATIONS

This application is based upon and claims the benefit of priority from Japanese Patent Application No. 2012-006038, filed Jan. 16, 2012, the entire contents of which are incorporated herein by reference.

FIELD

Embodiments described herein relate generally to an ultrasonic diagnostic apparatus, medical image processing apparatus, and medical image parallel display method.

BACKGROUND

A conventional ultrasonic diagnostic apparatus can display in real time how the heart beats or the fetus moves, by simply bringing an ultrasonic probe into contact with body surfaces. In addition, the ultrasonic diagnostic apparatus is highly safe as compared with other medical image diagnostic apparatuses, and hence allows repeated examinations. Furthermore, the ultrasonic diagnostic apparatus is smaller in size than other medical image diagnostic apparatuses such as an X-ray diagnostic apparatus, X-ray computed tomography apparatus, magnetic resonance imaging apparatus, and nuclear medicine diagnostic apparatus, and hence can be moved to the bedside to be easily and conveniently used for examinations. In addition, the ultrasonic diagnostic apparatus is free from exposure to X-rays and the like, and hence can be used in obstetric treatment, treatment at home, and the like.

Recently, with the development of high-frequency probes and advances in image processing techniques, the resolutions of ultrasonic diagnostic apparatuses have greatly improved. With this improvement in resolution, the use of ultrasonic diagnostic apparatuses has rapidly increased in the orthopedic field in recent years. For example, in diagnosis in orthopedic examinations, an ultrasonic diagnostic apparatus sometimes displays the two ultrasonic images, side by side in one window, which are generated by scanning the left and right corresponding regions of an object (for example, the arms or legs). That is, such an apparatus often displays left and right corresponding regions of an object side by side in one window to compare an affected side with a healthy side. In some cases, the apparatus displays the two ultrasonic images obtained by imaging a similar position of an affected region at different angles.

At this time, the apparatus laterally parallelly displays the two ultrasonic images on the display screen. When observing a mammary region and a superficial musculoskeletal region, in particular, the operator often turns his/her attention to a very shallow region with a depth of about 1 cm to 3 cm from the object surface, as shown in FIG. 8. In this case, to execute laterally parallel display, it is necessary to hide left and right end portions of display images by predetermined widths so as to fit them in the display areas on the display screen, as shown in, for example, FIG. 9. In addition, as shown in FIG. 10, to execute laterally parallel display with respect to the entire field angle of a scan range, it is necessary to reduce the ultrasonic images. In any case, nothing is displayed in the lower half region of the display screen. This raises the problem of ineffective use of the display screen.

An ultrasonic diagnostic apparatus is set in advance to display two ultrasonic images on the display screen either in the laterally parallel display mode or in the vertically parallel display mode. In order to set a desired parallel display mode, the operator needs to input information to change the setting via an input device. If the apparatus allows the operator to select between the laterally parallel display mode and the vertically parallel display mode, he/she needs to select one of the display modes via the input device. In examinations in ultrasonic diagnosis in orthopedic examination, there are demands for an ultrasonic diagnostic apparatus which allows easy operation with a sense of palpation. In the orthopedic field, there are many operators who are not familiar with the operation of an ultrasonic diagnostic apparatus. For this reason, there is an increasing need to complete an examination in ultrasonic diagnosis while avoiding elaborate button operations as much as possible. There is also an increasing need to minimize the number of buttons used in an input device. It is required to make a quick diagnosis in ultrasonic examination in orthopedic examination. For this reason, the operator often makes a diagnosis without performing elaborate operations for making settings for image display. In this case, the operator sometimes does not change the standard settings for image display and makes a diagnosis upon displaying the entire musculoskeletal organ while keeping each display area large.

As described above, when executing laterally parallel display and vertically parallel display of two ultrasonic images, the operator needs to execute elaborate button operations. In addition, although the display area of each ultrasonic image which is desired by the operator can greatly change in accordance with the state of an examination, the display area is not changed and remains the same. Furthermore, the operation of setting a display area imposes some burden on the operator.

BRIEF DESCRIPTION OF THE DRAWINGS

FIG. 2 is a block diagram showing an example of the arrangement of a scanning unit according to the first embodiment.

FIG. 4 is a flowchart showing a procedure for setting a specific display layout from a plurality of display layouts based on the aspect ratio of each generated ultrasonic image and the number of images to be simultaneously displayed according to the first embodiment.

FIG. 6 is a view showing an example of the arrangement of an ultrasonic diagnostic apparatus according to the second embodiment.

FIG. 10 is a view showing an example of ultrasonic images reduced to display the entire field angle of a scan range according to the conventional two image parallel display mode.

DETAILED DESCRIPTION

Figure 1:
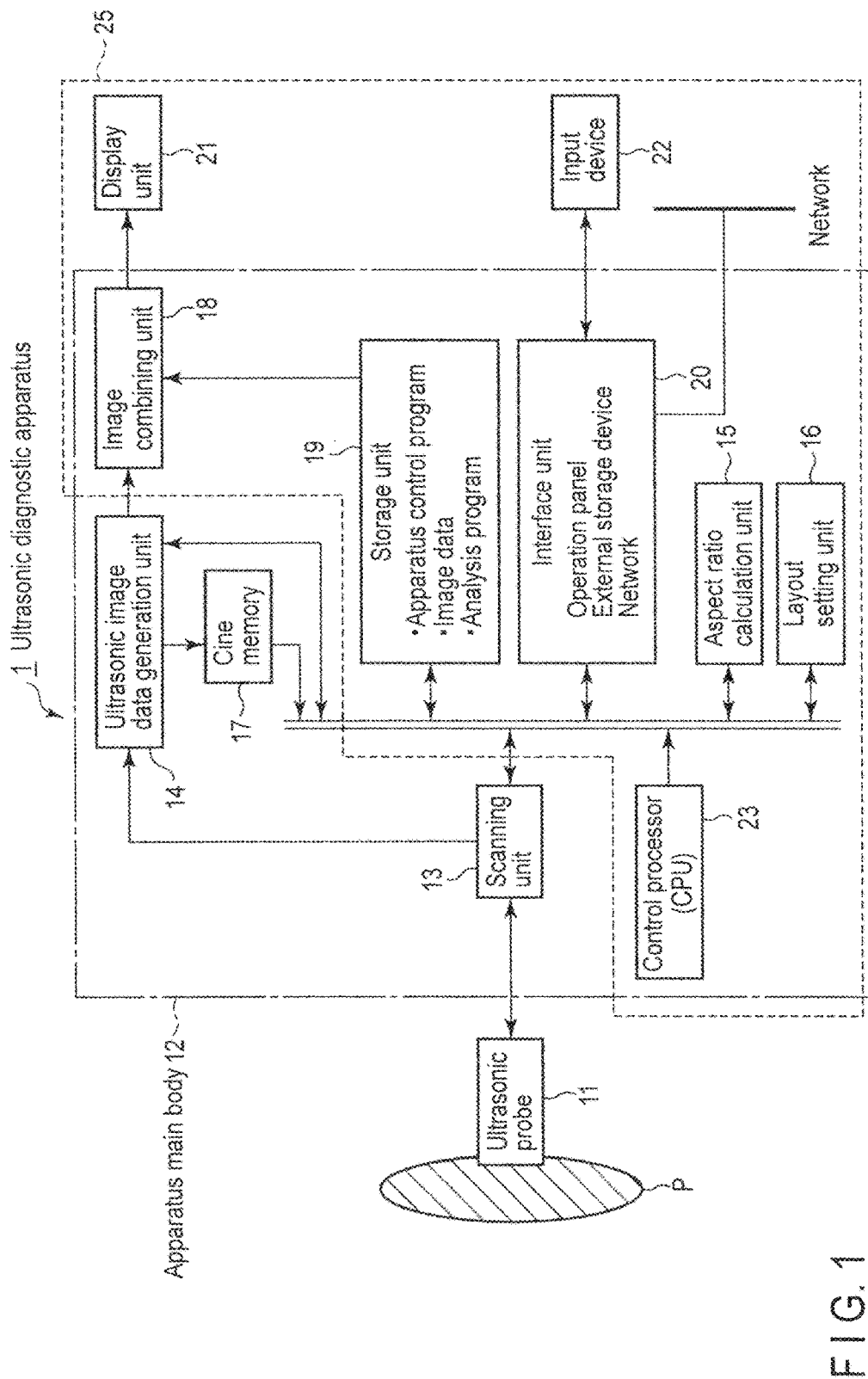
FIG. 1 is a block diagram showing the arrangement of an ultrasonic diagnostic apparatus according to the first embodiment.

In general, according to one embodiment, an ultrasonic diagnostic apparatus includes an ultrasonic probe, a scanning unit, a ultrasonic image data generation unit, a layout setting unit, and a display unit. The ultrasonic probe includes a plurality of transducers. The scanning unit scans an object with an ultrasonic beam via the ultrasonic probe. The ultrasonic image data generation unit generates data of a plurality of ultrasonic images based on outputs from the scanning unit. The layout setting unit sets a specific display layout based on an aspect ratio of a display frame of the ultrasonic image or a size of the ultrasonic image and the number of ultrasonic images displayed simultaneously. The display unit configured to display the ultrasonic images in accordance with the set display layout.

An ultrasonic diagnostic apparatus according to this embodiment will be described below with reference to the accompanying drawing. Note that the same reference numerals denote constituent elements having almost the same arrangements in the following description, and a repetitive description will be made only when required.

(First Embodiment)

FIG. 1 is a block diagram showing the arrangement of an ultrasonic diagnostic apparatus 1 according to the first embodiment. As shown in FIG. 1, the ultrasonic diagnostic apparatus 1 includes an ultrasonic probe 11, an apparatus main body 12, a display unit 21, and an input device 22 which is connected to the apparatus main body 12 and serves to input various kinds of instructions, commands, and information from the operator to the apparatus main body 12. In addition, a biological signal measurement unit (not shown) typified by an electrocardiograph, phonocardiograph, sphygmograph, or respiration sensor and a network may be connected to the ultrasonic diagnostic apparatus 1 via an interface unit 20. Note that the ultrasonic diagnostic apparatus 1 may include a position detection unit (not shown).

The ultrasonic probe 11 includes a plurality of piezoelectric transducers, a matching layer, and a backing member provided on the rear surface side of the plurality of piezoelectric transducers. The plurality of piezoelectric transducers are reversible acoustic/electric conversion elements such as piezoelectric ceramic elements. The plurality of transducers are juxtaposed and mounted on the distal end of the ultrasonic probe 11. Note that one piezoelectric transducer forms one channel.

Each transducer generates an ultrasonic wave in response to a driving signal supplied from an ultrasonic transmission unit 131 in a scanning unit 13 (to be described later). When the ultrasonic probe 11 transmits an ultrasonic wave to an object P, the transmitted ultrasonic wave (to be referred to as the transmission ultrasonic wave hereinafter) is sequentially reflected by a discontinuity surface of acoustic impedance of living tissue in the object. Each piezoelectric transducer receives the reflected ultrasonic waves and generates an echo signal. The amplitude of this echo signal depends on an acoustic impedance difference on the discontinuity surface, as a boundary, by which the echo signal is reflected. The frequency of the echo signal produced when a transmission ultrasonic wave is reflected by a moving blood flow, the surface of the cardiac wall, or the like is subjected to a frequency shift depending on the velocity component of the moving body (the blood flow and the surface of the cardiac wall) in the ultrasonic transmission direction due to the Doppler effect.

The ultrasonic probe 11 will be described below as a probe designed to perform two-dimensional scanning with a one-dimensional array. Note that the ultrasonic probe 11 may be a mechanical four-dimensional probe which executes three-dimensional scanning by swinging a one-dimensional array in a direction perpendicular to the array direction of a plurality of transducers. In addition, the ultrasonic probe 11 is not limited to a mechanical four-dimensional probe, and it is possible to use a two-dimensional array probe.

The matching layer is provided on the ultrasonic emitting surface side of the plurality of piezoelectric transducers to improve the efficiency of transmission/reception of ultrasonic waves to/from the object P. The backing member prevents ultrasonic waves from propagating backward from the piezoelectric transducers.

Note that the ultrasonic probe 11 may include a position sensor which acquires the position information of the ultrasonic probe 11 with reference to a predetermined position. The predetermined position is, for example, the position of the apparatus main body 12 of the ultrasonic diagnostic apparatus 1. Note that the predetermined position may be adjusted as needed in accordance with an instruction from the operator via the input device 22 (to be described later). For example, the position of the ultrasonic probe 11 set when an input from the input device 22 is received may be defined as the predetermined position. Note that the predetermined position may be the position where the probe comes into contact with the body surface of the object P for the first time.

The position detection unit detects the position of the ultrasonic probe 11 with reference to the predetermined position and the direction of the ultrasonic probe 11 by using the probe position information output from the position sensor. More specifically, the position detection unit decides the position and direction of the ultrasonic probe 11 on an absolute coordinate system with reference to the predetermined position. The position and direction of the ultrasonic probe 11 on the absolute coordinate system will be collectively referred to as probe coordinates hereinafter. The position detection unit outputs probe coordinates to an image generation unit 143 (to be described later).

The apparatus main body 12 includes the scanning unit 13, a ultrasonic image data generation unit 14, an aspect ratio calculation unit 15, a layout setting unit 16, a cine memory 17, an image combining unit 18, a storage unit 19, an interface unit 20, and a control processor (to be referred to as a CPU (Central Processing Unit) hereinafter) 23.

FIG. 2 is a view showing an example of the arrangement of the scanning unit 13. The scanning unit 13 includes the ultrasonic transmission unit 131 and an ultrasonic reception unit 132. The ultrasonic transmission unit 131 supplies a driving signal to each of the plurality of piezoelectric transducers of the ultrasonic probe 11 under the control of the CPU 23 (to be described later).

More specifically, the ultrasonic transmission unit 131 includes a pulse generator 131A, a transmission delay circuit 131B, and a pulser circuit 131C. The pulse generator 131A repeatedly generates rate pulses for the formation of transmission ultrasonic waves at a predetermined rate frequency fr Hz (period: 1/fr sec). The generated rate pulses are distributed in number corresponding to a channel count and sent to the transmission delay circuit 131B.

The transmission delay circuit 131B gives each rate pulse a delay time (to be referred to as a transmission delay time hereinafter) necessary to focus a transmission ultrasonic wave into a beam and determine transmission directivity for each of the plurality of channels. The storage unit 19 (to be described later) stores the transmission direction or transmission delay time of transmission ultrasonic waves (to be referred to as a transmission delay pattern hereinafter). The CPU 23 (to be described later) refers to the transmission delay pattern stored in the storage unit 19 at the time of transmission of ultrasonic waves. The pulses circuit 131C applies a voltage pulse (driving signal) to each of the plurality of transducers of the ultrasonic probe 11 at the timing based on this rate pulse. With this operation, an ultrasonic beam is transmitted to the object P.

The ultrasonic reception unit 132 includes a preamplifier 132A, an A/D (Analog to Digital) converter (not shown), a reception delay circuit 132B, and an adder 132C. The preamplifier 132A amplifies an echo signal received from the object P via the ultrasonic probe 11 for each channel. The A/D converter converts each amplified echo signal into a digital signal.

The reception delay circuit 132B gives the reception echo signals converted into digital signals delay times (to be referred to as reception delay times hereinafter) required to determine reception directivity. The storage unit 19 (to be described later) stores the reception direction or reception delay time of an echo signal (to be referred to as a reception delay pattern hereinafter). The CPU 23 (to be described later) refers to the reception delay pattern stored in the storage unit 19 at the time of reception of ultrasonic waves. The adder 132C adds a plurality of echo signals given the delay times. With this addition, the ultrasonic reception unit 132 generates a reception signal (to be also referred to as an RF (radiofrequency) signal) with a reflection component from a direction corresponding to the reception directivity being enhanced. The transmission directivity and the reception directivity determine the comprehensive directivity of ultrasonic transmission/reception. This comprehensive directivity determines an ultrasonic beam (so-called "ultrasonic scanning line").

Figure 3:
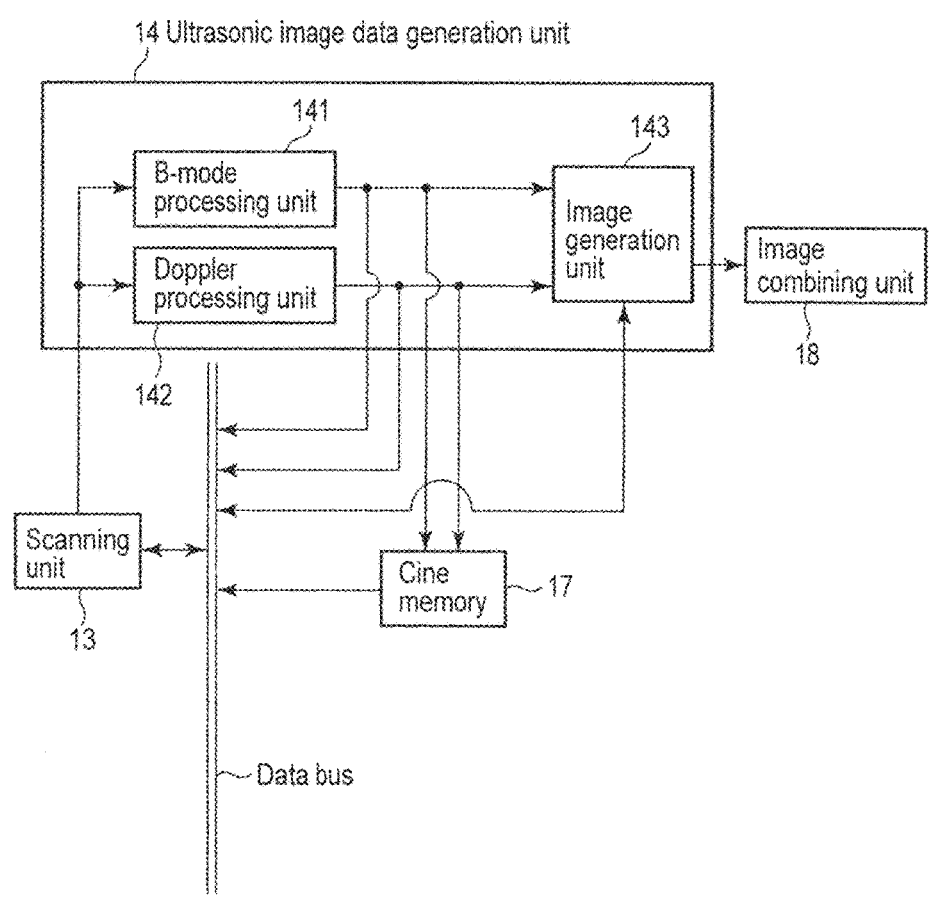
FIG. 3 is a block diagram showing an example of the arrangement of a ultrasonic image data generation unit according to the first embodiment.

FIG. 3 is a block diagram showing an example of the arrangement of the ultrasonic image data generation unit 14. The ultrasonic image data generation unit 14 includes a B-mode processing unit 141, a Doppler processing unit 142, and the image generation unit 143. The ultrasonic image data generation unit 14 generates ultrasonic image data. Ultrasonic image data includes raw data (to be described later). The ultrasonic image data is described later.

The B-mode processing unit 141 includes an envelope detector and a logarithmic converter (neither of which is shown). The envelope detector performs envelope detection of the reception signal output from the scanning unit 13. The envelope detector outputs the envelope-detected signal to the logarithmic converter (to be described later). The logarithmic converter relatively enhances a weak signal by logarithmically converting the envelope-detected signal. The B-mode processing unit 141 generates a signal value (B-mode data) for each depth on each scanning line or in each ultrasonic transmission/reception based on the signal enhanced by the logarithmic converter.

If the ultrasonic probe 11 is a mechanical four-dimensional probe or a two-dimensional array probe, the B-mode processing unit 141 generates three-dimensional B-mode data having a plurality of signal values respectively arranged in the azimuth direction, elevation direction, and depth direction (to be referred to as the range direction hereinafter) in a scanned region. The range direction is the depth direction on a scanning line. The azimuth direction is, for example, an electronic scanning direction along the array direction of one-dimensional ultrasonic transducers. The elevation direction is the mechanical swinging direction of the one-dimensional ultrasonic transducers.

Note that three-dimensional B-mode data may be data obtained by arranging a plurality of pixel values, a plurality of luminance values, or the like in the azimuth direction, elevation direction, and range direction, respectively, along scanning lines. In addition, three-dimensional B-mode data may be data concerning an ROI (Region Of Interest) set in advance in a scanned region. The B-mode processing unit 141 may generate volume data instead of three-dimensional B-mode data. The data generated by the B-mode processing unit 141 will be collectively referred to as B-mode data.

The Doppler processing unit 142 includes a mixer, LPF (Low Pass Filter), and velocity/variance/power computation device (none of which are shown). The mixer multiplies the reception signal output from the scanning unit 13 by a reference signal having a frequency $f_0$ equal to the transmission frequency. This multiplication obtains a signal having a component with a Doppler shift frequency $f_d$ and a signal having a frequency component of $(2f_0+f_d)$. The LPF removes a signal of a high-frequency component $(2f_0+f_d)$ from a signal having two types of frequency components from the mixer. By removing the signal of the high-frequency component $(2f_0+f_d)$, the Doppler processing unit 142 generates a Doppler signal having the component with the Doppler shift frequency $f_d$.

Note that the Doppler processing unit 142 may use a quadrature detection scheme to generate Doppler signals. In this case, the Doppler processing unit 142 performs quadrature detection to convert a reception signal (RF signal) into IQ signals. The Doppler processing unit 142 generates a Doppler signal having the Doppler shift frequency $f_d$ by performing complex Fourier transform on the IQ signals. Doppler signals are, for example, echo components due to a blood flow, tissue, and contrast medium.

The velocity/variance/power computation device includes an MTI (Moving Target Indicator) filter and an autocorrelation computation unit (neither of which is shown). The MTI filter removes a Doppler component (a clutter component) due to the respiratory movement or pulsatory movement of an organ or the like from a generated Doppler signal. The autocorrelation computation unit calculates the autocorrelation value of the Doppler signal obtained by extracting only blood flow information using the MTI filter. The autocorrelation computation unit calculates the average flow velocity value, a variance, the reflection intensity of the Doppler signal, and the like on the basis of the calculated autocorrelation value. The velocity/variance/power computation device generates color Doppler data from the average velocity value, the variance, the reflection intensity of the Doppler signal, and the like based on a plurality of Doppler signals. Doppler signals and color Doppler data will be collectively referred to as Doppler data hereinafter.

In addition, Doppler data and B-mode data will be collectively referred to as raw data. Note that raw data of an echo signal may be B-mode data based on harmonic components of transmission ultrasonic waves and elastic data concerning living tissue in the object. The B-mode processing unit 141 and the Doppler processing unit 142 output the generated raw data to the image generation unit 143.

Note that the B-mode processing unit 141 and the Doppler processing unit 142 may output the generated raw data to the aspect ratio calculation unit 15. Note that the B-mode processing unit 141 and the Doppler processing unit 142 can also output the generated raw data to a cine memory 17 (to be described later).

The image generation unit 143 includes a DSC (Digital Scan Converter) (not shown). The image generation unit 143 executes coordinate conversion processing (resampling) for the DSC. Coordinate conversion processing is to convert, for example, a scanning line signal string for ultrasonic scanning, which forms raw data, into a scanning line signal string in a general video format typified by a TV format. The image generation unit 143 executes interpolation processing following coordinate conversion processing for the DSC. Interpolation processing is to interpolate data between adjacent scanning line signal strings by using raw data in the scanning line signal strings.

The image generation unit 143 generates an ultrasonic image as a display image by executing coordinate conversion processing and interpolation processing for raw data. Note that the image generation unit 143 may have an image memory storing data (to be referred to as image data hereinafter) corresponding to the generated ultrasonic image. The image generation unit 143 outputs the image data to the aspect ratio calculation unit 15 and the image combining unit 18 (both of which will be described later). The ultrasonic image generated by using B-mode data will be referred to as a B-mode image hereinafter. In addition, an ultrasonic image generated by using Doppler data will be referred to as a Doppler image. In the following description, B-mode images and Doppler images will be collectively referred to as ultrasonic images.

Note that the image generation unit 143 may add the position information of a slice of the object P determined from the probe coordinates output from the position detection unit (not shown) to a generated ultrasonic image. The volume data generated in advance by other medical image apparatuses may be stored in the storage unit 19 to allow the image generation unit 143 to generate a medical image corresponding to a slice position of the ultrasonic image generated from the volume data and the position information of a slice of the object P.

The aspect ratio calculation unit 15 acquires the size of the display frame of the ultrasonic image displayed by the display unit 21 (to be described later). More specifically, when the operator inputs an instruction to execute two-image parallel display via the input device 22, the aspect ratio calculation unit 15 acquires the longitudinal and transverse lengths of the display frame of each displayed ultrasonic image. An instruction to execute two-image parallel display is issued when, for example, the operator operates an input button of the image parallel display mode of juxtaposing and displaying two medical images. Note that the image parallel display mode is not limited to two images. The image parallel display mode can juxtapose an arbitrary number of images. Note that the information input via the input device 22 may be the number of images to be simultaneously juxtaposed and displayed (to be referred to as the number of images displayed simultaneously hereinafter) instead of information instructing two image parallel display. In addition, the number of images displayed simultaneously is not limited to two. For the sake of simplicity, assume that the number of images displayed simultaneously input via the input device 22 is two. The aspect ratio calculation unit 15 may acquire the size of the display frame of each ultrasonic image generated by the image generation unit 143. In addition, the aspect ratio calculation unit 15 may acquire the display size of the medical image generated by the image generation unit 143 instead of an ultrasonic image. Note that the above medical image may be used to set a layout (to be described later).

The aspect ratio calculation unit 15 calculates the ratio of the longitudinal length of each display size to the transverse length of the display size (to be referred to as the aspect ratio hereinafter). Note that the aspect ratio calculation unit 15 may calculate the ratio of the transverse length to the longitudinal length. The aspect ratio calculation unit 15 outputs the calculated aspect ratio to the layout setting unit 16 (to be described later). Note that the aspect ratio calculation unit 15 may acquire, as an aspect ratio, the number of pixels corresponding to the size of the display frame of each ultrasonic in the longitudinal direction and the number of pixels corresponding to the size in the lateral direction. In this case, the aspect ratio calculation unit 15 calculates the ratio of the number of pixels in the longitudinal direction to that in the lateral direction as an aspect ratio. If an ultrasonic image is enlarged and displayed, the aspect ratio calculation unit 15 calculates the aspect ratio of the display area of the enlarged/displayed ultrasonic image.

The layout setting unit 16 stores a threshold corresponding to the number of images displayed simultaneously (to be referred to as a simultaneous display threshold hereinafter) in a memory (not shown). When the number of images displayed simultaneously is input via the input device 22, the layout setting unit 16 reads out a simultaneous display threshold corresponding to the number of images displayed simultaneously from the memory. The layout setting unit 16 compares the aspect ratio with the simultaneous display threshold. Note that the simultaneous display threshold may be stored in the storage unit 19 (to be described later).

If, for example, the aspect ratio is equal to or more than the simultaneous display threshold, the layout setting unit 16 sets a specific display layout of the plurality of display layouts stored in the storage unit 19 in advance as a layout for the display of a plurality of ultrasonic images. The plurality of display layouts include, for example, a display layout for n (n is an integer equal to or more than 2) images juxtaposed laterally and a display layout for m (m is an integer equal to or more than 2) images juxtaposed vertically. The specific display layout is, for example, a display layout (to be referred to as a laterally parallel layout hereinafter) for the display of laterally parallel two images. The layout setting unit 16 outputs, to the CPU 23 (to be described later), an instruction to output the set laterally parallel layout from the storage unit 19 to the image combining unit 18.

If the aspect ratio is less than the threshold, the layout setting unit 16 sets a specific display layout from the plurality of display layouts stored in the storage unit 19. The specific display layout is, for example, a display layout (to be referred to a vertically parallel layout hereinafter) for the display of vertically parallel two images. The layout setting unit 16 outputs, to the CPU 23 (to be described later), an instruction to output the set vertically parallel layout from the storage unit 19 to the image combining unit 18.

Note that the above description concerns a case in which the aspect ratio is the ratio of a longitudinal length to a transverse length. If the ratio of a transverse length to a longitudinal length is used as an aspect ratio, the above description will be reworded as follows.

If the aspect ratio is equal to or more than the simultaneous display threshold, the layout setting unit 16 sets the vertically parallel layout of the plurality of display layouts as a layout for the display of a plurality of ultrasonic images. The layout setting unit 16 outputs, to the CPU 23 (to be described later), an instruction to output the set vertically parallel layout from the storage unit 19 to the image combining unit 18. If the aspect ratio is less than the simultaneous display threshold, the layout setting unit 16 sets the laterally parallel layout of the plurality of display layouts stored in the storage unit 19, as a layout for the display of a plurality of ultrasonic images. The layout setting unit 16 outputs, to the CPU 23 (to be described later), an instruction to output the set laterally parallel layout from the storage unit 19 to the image combining unit 18.

Note that the layout setting unit 16 can set a specific display layout based on the size of each ultrasonic image and the number of ultrasonic images display simultaneously. The size of a ultrasonic image includes the longitudinal and transverse lengths of the display frame of a ultrasonic image. More specifically, the layout setting unit 16 specifies a shorter one of the longitudinal and transverse lengths. The layout setting unit 16 sets a display layout for parallel display of a plurality of ultrasonic images equal to the input number of images displayed simultaneously concerning the direction of the shorter length (longitudinal or lateral) as a layout for the display of a plurality of ultrasonic images.

Note that the layout setting unit 16 may perform the operation of calculating and generating a specific display layout based on information about the aspect ratio and the number or images displayed simultaneously instead of the operation of setting a specific display layout from the plurality of display layouts stored in advance.

The layout setting unit 16 can also set a specific display layout based on the azimuth angle or image width of each ultrasonic image, the visual field depth of each ultrasonic image, and the number of images displayed simultaneously. The operation of setting a specific display layout based on the azimuth angle of each ultrasonic image, the visual field depths of the ultrasonic image, and the number of images displayed simultaneously will be described below.

If each ultrasonic image is a B-mode image having a sectorial shape, the layout setting unit 16 acquires the visual field depth and azimuth angle of the ultrasonic image from the scanning unit 13. If the visual field depth is large and the azimuth angle is small, the layout setting unit 16 sets the laterally parallel layout as a layout for the display of a plurality of ultrasonic images. If the visual field depth is small and the azimuth angle is large, the layout setting unit 16 sets the vertically parallel layout as a layout for the display of a plurality of ultrasonic images.

The operation of setting a specific display layout based on the image width of each ultrasonic image, the visual field depth of the ultrasonic image, and the number of images displayed simultaneously will be described next. An image width is equivalent to the width of a ultrasonic image if the ultrasonic probe 11 is a linear probe having transducers linearly arrayed one-dimensionally.

The layout setting unit 16 acquires the visual field depth and image width of each ultrasonic image from the scanning unit 13. If the visual field depth is large and the image width is small, the layout setting unit 16 sets the laterally parallel layout as a layout for the display of a plurality of ultrasonic images. If the visual field depth is small and the image width is large, the layout setting unit 16 sets the vertically parallel layout as a layout for the display of a plurality of ultrasonic images.

The layout setting unit 16 may also set a specific display layout based on diagnostic parameters such as the central frequency (to be referred to as the transmission frequency hereinafter) of ultrasonic waves transmitted to the object P. More specifically, the layout setting unit 16 stores a threshold (to be referred to as a frequency threshold hereinafter) for transmission frequencies in a memory (not shown). The layout setting unit 16 compares a transmission frequency with the frequency threshold. If the transmission frequency is higher than the frequency threshold, the layout setting unit 16 sets the vertically parallel layout as a specific display layout. If the transmission frequency is higher than the frequency threshold, vertically parallel display is executed concerning shallow portions of ultrasonic images. The frequency threshold is a frequency which is used when a region of the object P is imaged up to a predetermined depth from each transducer.

Note that a frequency threshold and a transmission frequency may be input via the input device 22 (to be described later). While laterally parallel display is already performed, the layout setting unit 16 may set the vertically parallel layout as a specific display layout in response to setting or inputting of a transmission frequency higher than the frequency threshold.

The cine memory 17 is a memory which stores ultrasonic images corresponding to a plurality of frames immediately before freezing. Continuously displaying (cine displaying) the images stored in this cine memory can display a moving ultrasonic image.

The image combining unit 18 combines an ultrasonic image with the character information of various parameters, scale marks, and the like. The image combining unit 18 outputs the combined ultrasonic image to the display unit 21. The image combining unit 18 generates parallel images by juxtaposing and displaying the ultrasonic image used to calculate an aspect ratio and the ultrasonic image generated by the image generation unit 143 in accordance with the specific display layout output from the storage unit 19. For example, the ultrasonic image used to calculate an aspect ratio is an ultrasonic image, out of the ultrasonic images displayed or updated in real time, which corresponds to freezing operation or parallel display operation performed via the input device 22. The ultrasonic image generated by the image generation unit 143 is, for example, an ultrasonic image displayed or updated in real time. Note that the image combining unit 18 may generate parallel images by juxtaposing and displaying the ultrasonic image used to calculate (the ultrasonic image updated in real time) an aspect ratio and the image stored in the cine memory 17 in accordance with the specific display layout output from the storage unit 19. At this time, the image stored in the cine memory is cine-displayed (loop-reproduced).

Note that two types of ultrasonic images of parallel images may be ultrasonic images in different modes. For example, the ultrasonic image used to calculate an aspect ratio may be a B-mode image corresponding to freezing operation or parallel display operation performed via the input device 22. The image generated by the image generation unit 143 may be a Doppler image. The image combining unit 18 outputs the generated parallel images to the display unit 21 (to be described later).

Note that the image combining unit 18 may generate parallel images by juxtaposing and displaying the ultrasonic image used to calculate an aspect ratio and the medical image, out of a plurality of medical images concerning the object P, which is selected by the operator. A medical image is a past medical image of the object P which has been generated by other medical image diagnostic apparatuses such as an X-ray diagnostic apparatus, X-ray computed tomography apparatus, magnetic resonance imaging apparatus, and nuclear medicine diagnostic apparatus. Note that the image combining unit 18 may generate parallel images by juxtaposing and displaying the ultrasonic image used to calculate an aspect ratio and a medical image corresponding to a slice position of the ultrasonic image used to calculate the aspect ratio, in accordance with the specific display layout output from the storage unit 19. A medical image of the same slice as that of the generated ultrasonic image may be downloaded from another medical image diagnostic apparatus or a PACS (Picture Archiving and Communication System) via the interface unit 20 (to be described later).

The storage unit 19 stores pluralities of reception delay patterns and transmission delay patterns with different focus depths, control programs for the ultrasonic diagnostic apparatus 1, a diagnostic protocol, various data groups such as transmission/reception conditions, the raw data and ultrasonic images generated by the image generation unit 14, an algorithm concerning the calculation of an aspect ratio, a plurality of display layouts, a plurality of medical images and volume data concerning the object P which are generated by other medical image diagnostic apparatuses, a plurality of past medical images of the object P which correspond to the slice position of a generated ultrasonic image, an algorithm for generating a medical image corresponding to the slice position of the ultrasonic image generated by using stored volume data and the position information of an object slice, a simultaneous display threshold, and the like.

The interface unit 20 is an interface concerning the input unit 22, a network, an external storage device (not shown), and a biological signal measurement unit (not shown). Data such as ultrasonic images, analysis results, and the like obtained by the apparatus main body 12 can be transferred to other apparatuses via the interface unit 20 and the network. The interface unit 20 can also download the medical images concerning the object P which are acquired by other medical image diagnostic apparatuses (not shown) via the network.

The display unit 21 displays ultrasonic images such as B-mode images and Doppler images or parallel images based on outputs from the image combining unit 18. Note that the display unit 21 may execute adjustments concerning brightness, contrast, dynamic range, γ correction, and the like and color mapping for displayed images.

The input device 22 is connected to the interface unit 20 and inputs various instructions, commands, information, selections, and settings from the operator to the apparatus main body 12. The input device 22 includes input devices such as a trackball, switch buttons, mouse, and keyboard (none of which are shown). The input device detects the coordinates of a cursor displayed on the display screen, and outputs the detected coordinates to the CPU 23. Note that the input device may be a touch command screen provided to cover the display screen. In this case, the input device 22 detects touched and designated coordinates by a coordinate reading principle such as an electromagnetic induction scheme, magnetostriction scheme, or a pressure-sensitive scheme, and outputs the detected coordinates to the CPU 23. When, for example, the operator operates the end button or freeze button of the input device 22, the ultrasonic transmission/reception is terminated, and the apparatus main body 12 is set in a pause state.

The input device 22 inputs adjustments of a predetermined position, instructions concerning the image parallel display modes, the number of images displayed simultaneously, and the like to the apparatus main body 12. An input device includes, for example, a button for inputting an image parallel display mode (to be referred to as an image parallel display mode input button hereinafter).

When the operator presses the image parallel display mode input button while one ultrasonic image or ultrasonic image is displayed on the display unit 21, the number of ultrasonic images to be displayed on the display unit 21 is switched from one to a plural number (e.g., two). With this switching operation, the display unit 21 displays a plurality of ultrasonic images in the specific display layout set by the layout setting unit 16.

While two ultrasonic images are displayed in the vertically parallel layout, the input device 22 can increase the longitudinal length (to be referred to as the display depth hereinafter) of the display frame of one ultrasonic image by an arbitrary length. When the display depth is changed, the layout setting unit 16 calculates the aspect ratio of the display frame after the change. An aspect ratio is defined by the value obtained by dividing the longitudinal length by the transverse length. If the aspect ratio is high, the display frame becomes longitudinally long. An aspect ratio is a parameter indicating the longitudinally long shape of a display frame. Assume that when the display depth is increased, the aspect ratio of the display frame exceeds a predetermined threshold, and the longitudinal length of the display frame becomes longer than the transverse length. In this case, the layout setting unit 16 sets the laterally parallel layout as a specific display layout. The display unit 21 displays two ultrasonic images in the laterally parallel layout having the increased display depth. At this time, the display depth of the other ultrasonic image becomes equal to the increased display depth. In contrast to the above operation, when the aspect ratio becomes lower than a predetermined value as the operator decreases the display depth, the layout setting unit 16 sets the vertically parallel layout as a specific display layout.

While two ultrasonic images are displayed in the laterally parallel layout, the input device 22 can input an instruction to enlarge and display (e.g., a ZOOM instruction) part of one ultrasonic image. When an enlarged display instruction is input, the layout setting unit 16 calculates the aspect ratio of the display frame after enlargement. If the aspect ratio of the enlarged display area is lower than a predetermined threshold and the longitudinal length of the display frame is shorter than the transverse length, the layout setting unit 16 sets the vertically parallel layout as a specific display layout. The display unit 21 displays parts of the two ultrasonic images which are enlarged at the same magnification. That is, part of the other ultrasonic image which corresponds to part of one ultrasonic image is enlarged at the same magnification as that of part of one ultrasonic image and is displayed together with part of one ultrasonic image in the vertically parallel layout. In contrast to the above operation, if the aspect ratio of the display area exceeds a predetermined value upon enlarged display, the layout setting unit 16 sets the laterally parallel layout as a specific display layout.

Note that the above embodiment has exemplified the case in which the layout setting unit 16 decides a specific display layout in response to when the longitudinal length of the display frame becomes longer or shorter than the transverse length. However, the embodiment is not limited to this case. It is also possible to set an aspect ratio threshold in advance to make the layout setting unit 16 select the vertically parallel layout even if the display frame has a longitudinally long shape.

The CPU 23 reads out a transmission delay pattern, reception delay pattern, and apparatus control program from the storage unit 19 based on the selection between the B mode and the Doppler mode, frame rate, scanned depth, and start/end of transmission which are input by the operator via the input device 22. The CPU 23 controls the apparatus main body 12 and the ultrasonic probe 11 in accordance with the readout transmission delay patter, reception delay pattern, apparatus control program, and the like. For example, the CPU 23 controls the aspect ratio calculation unit 15 in accordance with an algorithm concerning the calculation of an aspect ratio, which is read out. The CPU 23 reads out, from the storage unit 19, the specific display layout set by the layout setting unit 16 from a plurality of display layouts. The CPU 23 outputs the readout specific display layout to the image combining unit 18.

(Image Parallel Display Function)

The image parallel display function is a function of setting a specific display layout from a plurality of display layouts based on a simultaneous display threshold corresponding to the number of images displayed simultaneously and the aspect ratio of each ultrasonic and parallelly displaying the ultrasonic image used to calculate the aspect ratio and a selected medical image in accordance with the set specific display layout. Processing concerning the image parallel display function (to be referred to as image parallel display processing hereinafter) will be described.

FIG. 4 is a flowchart showing a procedure for image parallel display function.

The apparatus transmits ultrasonic waves to the object P to generate an ultrasonic image of a slice of the object P (step Sa1). The display unit 21 displays the generated ultrasonic image. The operator inputs an image parallel display mode and the number of images displayed simultaneously via the input device 22 (step Sa2). At this time, the operator may select a medical image to be simultaneously displayed via the input device 22. The apparatus calculates the aspect ratio of the display frame of each ultrasonic image (step Sa3). The apparatus sets a specific display layout from a plurality of display layouts based on the calculated aspect ratio, the input number of images displayed simultaneously, and simultaneous display threshold (step Sa4). The display unit 21 displays the displayed ultrasonic image and the selected medical image in accordance with the set specific display layout (step Sa5).

Figure 5:
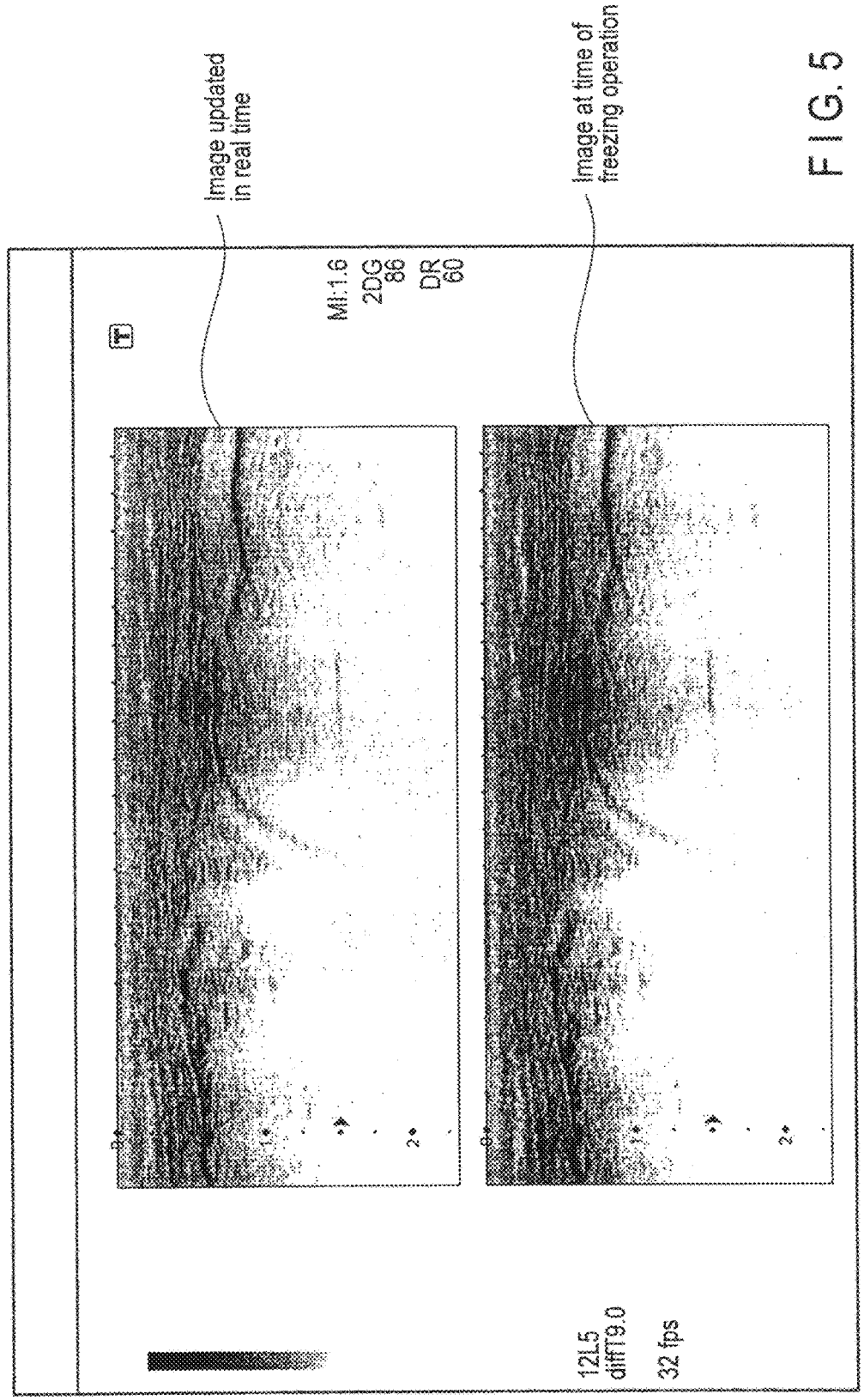
FIG. 5 is a view showing an example of display of two ultrasonic images in a specific display layout according to the first embodiment.

FIG. 5 is a view showing an example of two ultrasonic images displayed by the display unit 21 in the specific display layout (vertically parallel layout) in the processing in step Sa5. In the vertically parallel layout in FIG. 5, the upper ultrasonic image indicates an image updated in real time. In the vertically parallel layout in FIG. 5, the lower ultrasonic image indicates an ultrasonic image at the time of freezing operation or parallel display operation.

(Modification)

This modification differs from the first embodiment in that when an ultrasonic image displayed by the display unit 21 is enlarged and displayed via the input device 22, an aspect ratio is calculated by using the size of the display frame of the enlarged and displayed ultrasonic image.

The input device 22 inputs an instruction to enlarge and display (ZOOM: to be referred to as an enlarged display instruction hereinafter) one ultrasonic image displayed on the display unit 21. Note that the input device 22 may input an instruction to move (PAN: to be referred to as a display area move instruction hereinafter) the display area of one ultrasonic image displayed on the display unit 21.

The display unit 21 enlarges and displays a displayed ultrasonic image in response to the input of an enlarged display instruction. The display unit 21 moves the display area of a displayed ultrasonic image in response to the input of a display area move instruction.

When the operator inputs an instruction to execute two image parallel display via the input device 22 while the display unit 21 displays enlarged and displayed ultrasonic images (to be referred to as enlarged and displayed images hereinafter), the aspect ratio calculation unit 15 acquires the size of the display frame of each enlarged and displayed image. When the operator inputs an instruction to execute two image parallel display via the input device 22 while ultrasonic images whose display areas have been moved (to be referred to as display-area-moved images hereinafter), the aspect ratio calculation unit 15 may acquire the display size of each display-area-moved image. For the sake of simplicity, the processing executed for enlarged and displayed images by the aspect ratio calculation unit 15 will be described below.

More specifically, the aspect ratio calculation unit 15 acquires the longitudinal and transverse lengths of the display frame of each enlarged and displayed image displayed by the display unit 21. The aspect ratio calculation unit 15 calculates an aspect ratio by using the acquired longitudinal and transverse lengths. The aspect ratio calculation unit 15 outputs the calculated aspect ratio to the layout setting unit 16.

(Image Parallel Display Function)

This function differs from the image parallel display function in the first embodiment in that the following processing is inserted between the processing in step Sa1 and the processing in step Sa2 in the flowchart of FIG. 4, and the processing in step Sa3 is changed as follows.

The processing inserted between the processing in step Sa1 and the processing in step Sa2 is the processing of enlarging and displaying ultrasonic images via the input device 22.

The processing in step Sa3 is changed to the processing of calculating the aspect ratio of the display frame of each enlarged and displayed ultrasonic image.

The arrangement described above can obtain the following effects.

The ultrasonic diagnostic apparatus 1 can set a specific display layout optimal for parallel display from a plurality of display layouts based on the aspect ratio of the display frame of each displayed ultrasonic image and the number of images displayed simultaneously and display a plurality of ultrasonic images in accordance with the set specific display layout. With this operation, once the operator inputs an image parallel display mode, he/she need not input any additional elaborate instructions, thus greatly improving operability. In addition, it is possible to display a plurality of ultrasonic images in response to an instruction from the operator while maintaining the display area of each enlarged ultrasonic image.

The ultrasonic diagnostic apparatus 1 allows to set a display layout optimal for image parallel display without changing the presets in an image parallel display mode. This improves examination efficiency in ultrasonic diagnosis in an orthopedic department and a rheumatism department, in which various regions are observed. In addition, the ultrasonic diagnostic apparatus 1 allows even an operator who is unskilled in operating the ultrasonic diagnostic apparatus 1 to execute image parallel display in the same manner as a skilled operator because the number of button operations by the operator is small.

In addition, the ultrasonic diagnostic apparatus 1 can set a display layout based on diagnostic parameters such as an azimuth angle, visual field depth, and transmission frequency. This reduces button operations via the input device 22 and hence allows even an operator who is unskilled in operating the ultrasonic diagnostic apparatus 1 to execute image parallel display in the same manner as a skilled operator.

Furthermore, according this ultrasonic diagnostic apparatus, when the display depth of one of two ultrasonic images displayed in the vertically parallel layout is increased to such an extent that the aspect ratio of the display area becomes equal to or more than a predetermined value, it is possible to set the laterally parallel layout with the increased display depth. This makes it possible to automatically set a specific display layout from the vertically parallel layout to the laterally parallel layout in accordance with a change in the size of each displayed image even while the images are parallelly displayed.

Moreover, according to this ultrasonic diagnostic apparatus, when the operator inputs an enlarged display instruction for part of one of two ultrasonic images displayed in the laterally parallel layout and the aspect ratio of the enlarged and displayed area becomes equal to or less than a predetermined value, the vertically parallel layout is set. This can display the two ultrasonic images enlarged at the same magnification in the vertically parallel layout.

(Second Embodiment)

The second embodiment differs from the first embodiment in that the apparatus decides part of a ultrasonic image displayed by a display unit 21 as a display area based on the image data or raw data generated by a ultrasonic image data generation unit 14, sets a specific display layout from a plurality of display layouts based on the aspect ratio of the decided display area and the number of images displayed simultaneously, and displays the ultrasonic images in the decided display areas in accordance with the set specific display layout.

FIG. 6 is a block diagram showing an example of the arrangement of an ultrasonic diagnostic apparatus according to the second embodiment.

A display area decision unit 24 decides a display area for each ultrasonic image based on the image data of the ultrasonic image output from the ultrasonic image data generation unit 14.

For example, the display area decision unit 24 compares a plurality of pixels in the generated ultrasonic image with the first threshold. The display area decision unit 24 specifies a plurality of pixels having pixel values smaller than the first threshold. The display area decision unit 24 specifies the length (or the number of pixels) by which specified pixels continue from the lower end of the ultrasonic image for each of a plurality of columns (to be referred to as a plurality of pixel columns hereinafter) constituted by a plurality of pixels arranged parallel in the longitudinal direction of the ultrasonic image. The display area decision unit 24 subtracts the shortest one of a plurality of lengths respectively corresponding to a plurality of pixel columns from the longitudinal length of the ultrasonic image. The length obtained by this subtraction will be referred to as the first difference length. The display area decision unit 24 decides a position spaced apart from the upper end of a ultrasonic image by the first difference length as the lower end of the display area of the ultrasonic image. The display area decision unit 24 decides the left and right ends of the ultrasonic image as the left and right ends of the display area, and decides the upper end of the ultrasonic image as the upper end of the display area.

The display area decision unit 24 outputs a plurality of pixels included in the display area of a ultrasonic image as a ultrasonic display image to a cine memory 17, a storage unit 19, and the display unit 21. The display area decision unit 24 deletes pixels which are not included in the display area of the ultrasonic image. Note that the display area decision unit 24 may store pixels which are not included in the display area of the ultrasonic image as a non-display area in the storage unit 19. At this time, the display area decision unit 24 can also generate an original ultrasonic image by combining the ultrasonic display image with the non-display area.

The display area decision unit 24 may use a luminance value or a value concerning hue instead of a pixel value. In this case, the display area decision unit 24 uses a second threshold different from the first threshold. Note that the display area decision unit 24 can also decide a display area for the raw data of each ultrasonic image displayed in an image parallel display mode by comparing the raw data on a scanning line with a third threshold different from the first and second thresholds.

Note that the display area decision unit 24 specifies the length (or the number of pixels) by which specified pixels continue from the left end of a ultrasonic image for each of a plurality of rows (to be referred to as a plurality of pixel rows hereinafter) constituted by a plurality of pixels arranged parallel in the transverse axis of the ultrasonic image. The display area decision unit 24 subtracts the shortest one of a plurality of lengths respectively corresponding to a plurality of pixel rows from the length of the transverse axis of the ultrasonic image. The length obtained by this subtraction will be referred to as the second difference length. The display area decision unit 24 may decide a position spaced apart from the left end of a ultrasonic image by the second difference length as the left end of the display area of the ultrasonic image.

In addition, the display area decision unit 24 specifies the length (or the number of pixels) by which specified pixels continue from the right end of a ultrasonic image for each of a plurality of pixel rows. The display area decision unit 24 subtracts the shortest one of a plurality of lengths respectively corresponding to a plurality of pixel rows from the length of the transverse axis of the ultrasonic image. The length obtained by this subtraction will be referred to as the third difference length. The display area decision unit 24 may decide a position spaced apart from the right end of a ultrasonic image by the third difference length as the right end of the display area of the ultrasonic image.

An aspect ratio calculation unit 15 acquires the size of the display area of the ultrasonic image decided by the display area decision unit 24. The aspect ratio calculation unit 15 calculates the ratio (aspect ratio) of the longitudinal length of the display area to the transverse length of the display area.

The storage unit 19 stores one of the first to third thresholds which corresponds to a method of deciding a display area.

(Image Parallel Display Function)

The image parallel display function is a function of deciding part of a ultrasonic image displayed by the display unit 21 as a display area based on generated ultrasonic image data or raw data, setting a specific display layout from a plurality of display layouts based on the aspect ratio of the decided display area and the number of images displayed simultaneously, and displaying the ultrasonic image in the decided display area in accordance with the set specified display layout. Processing concerning the image parallel display function will be described below.

Figure 7:
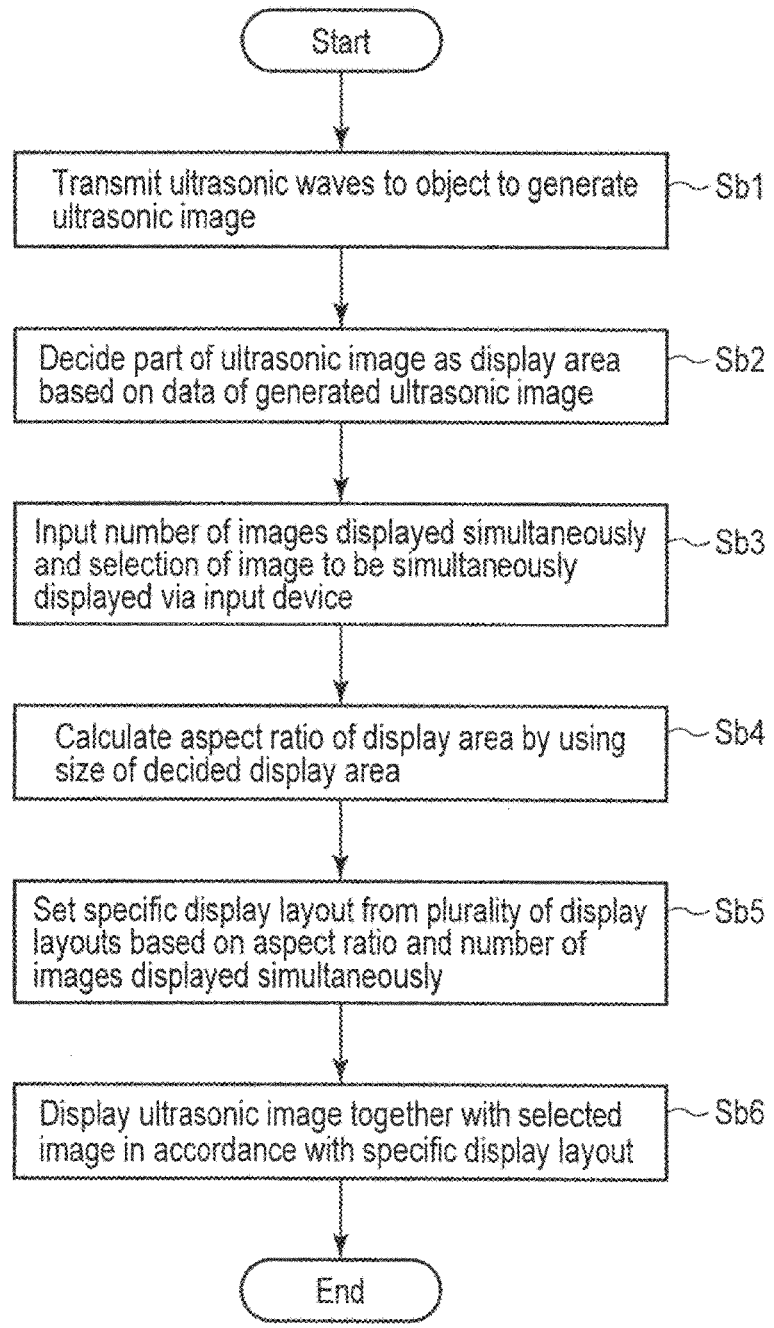
FIG. 7 is a flowchart showing a procedure for deciding the display area of each generated ultrasonic image based on the data of the ultrasonic image and setting a specific display layout from a plurality of display layouts based on the aspect ratio of the decided display area and the number of images to be simultaneously displayed according to the second embodiment.
Figure 8:
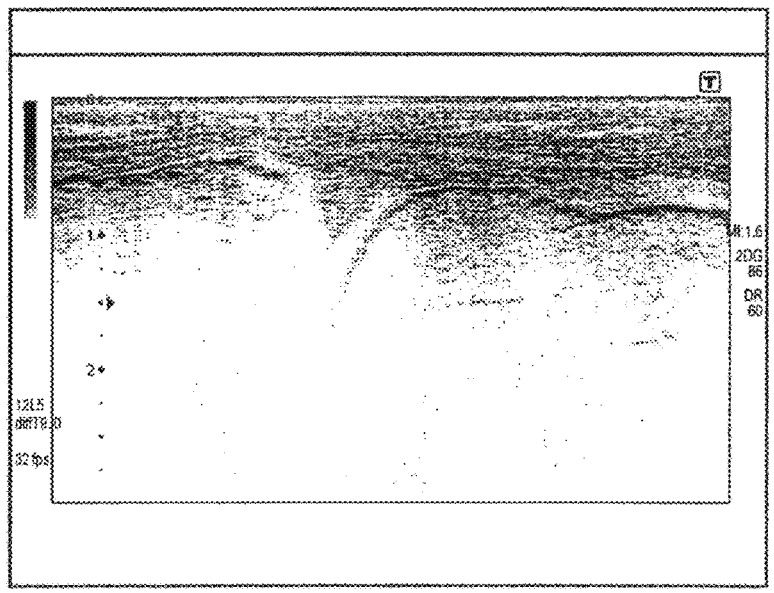
FIG. 8 is a view showing an example of a conventional ultrasonic image.
Figure 9:
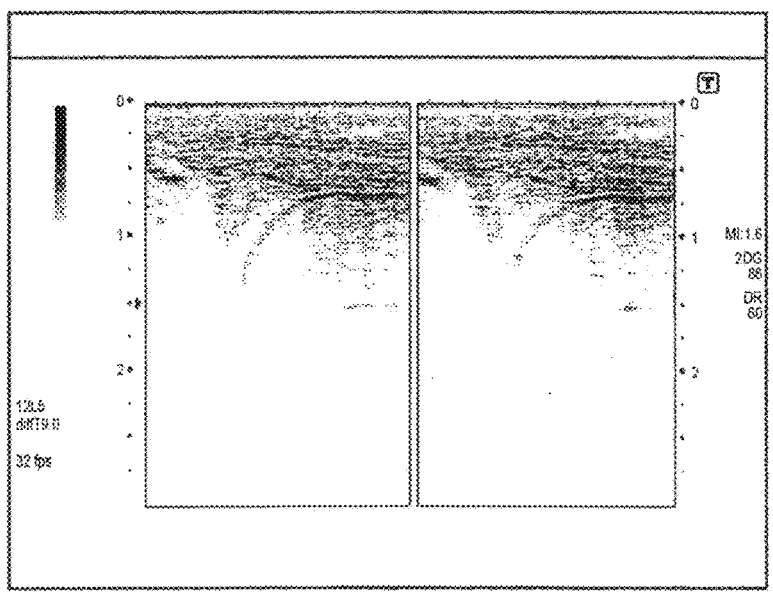
FIG. 9 is a view showing an example of ultrasonic images with left and right end portions of the display images being hidden according to the conventional two image parallel display mode.

FIG. 7 is a flowchart showing a procedure for deciding part of a ultrasonic image as a display area based on generated ultrasonic image data, and setting a specific display layout from a plurality of display layouts based on the aspect ratio of the decided display area and the number of images displayed simultaneously according to the second embodiment.

The apparatus transmits ultrasonic waves to the object P to generate ultrasonic image data (step Sb1). The apparatus then decides part of a ultrasonic image as a display area based on the generated ultrasonic image data (step Sb2). The operator inputs an image parallel display mode and the number of images displayed simultaneously via the input device 22 (step Sb3). At this time, a medical image to be simultaneously displayed may be selected via an input device 22. The apparatus calculates the aspect ratio of the display area (step Sb4). The apparatus sets a specific display layout from a plurality of display layouts based on the aspect ratio of the display area and the input number of images displayed simultaneously (step Sb5). The display unit 21 displays the ultrasonic image and the selected medical image in accordance with the set specific display layout (step Sb6).

(Modification)

This modification differs from the second embodiment in that the apparatus calculates the ratio (S/N ratio (Signal to Noise ratio)) of the ultrasonic image generated by the ultrasonic image data generation unit 14 to the noise image stored in the storage unit 19 in advance for each pixel, and decides a display area by using the calculated S/N ratios and the fourth threshold.

The storage unit 19 stores a noise image. A noise image is an image generated by executing only reception processing without transmitting any ultrasonic waves to the object. Note that a noise image may be an image concerning white noise which is generated by using normal random numbers. The storage unit 19 stores the fourth threshold. The fourth threshold is used by the display area decision unit 24 (to be described later) to decide the display area of a ultrasonic image. Note that a noise image may be read from a PACS connected via an interface unit 20 and a network. The storage unit 19 stores the read noise image.

The display area decision unit 24 reads out the noise image stored in the storage unit 19. The display area decision unit 24 calculates the S/N ratio of an ultrasonic image relative to the readout noise image for each pixel. More specifically, the display area decision unit 24 calculates the ratio of the pixel value of each pixel of the ultrasonic image to that of a corresponding pixel, of the noise image, which has the same coordinates. The display area decision unit 24 compares the S/N ratio with the fourth threshold for each pixel. The display area decision unit 24 specifies a plurality of pixels concerning S/N ratios lower than the fourth threshold in the ultrasonic image. The subsequent processing is the same as that in the second embodiment, and hence a description of it will be omitted.

Note that the display area decision unit 24 can also use the luminance values of the ultrasonic image displayed by the display unit 21 instead of the pixel values of the ultrasonic image. At this time, the display area decision unit 24 uses the luminance values of the noise image displayed by the display unit 21 instead of the pixel values of the noise image. The display area decision unit 24 can also use the raw data of an ultrasonic image instead of the pixel values of the ultrasonic image. In addition, the display area decision unit 24 may compare S/N ratios for, for example, each block of 3 pixels×3 pixels instead of comparing S/N ratios for each pixel. The value of an S/N ratio as a comparison target may be the value of the S/N ratio of the center of each block or the average value of the S/N ratios of the respective pixels in each block.

(Image Parallel Display Function)

This function differs from the display parallel display function in the second embodiment in that it calculates an S/N ratio for each pixel based on ultrasonic image data or raw data and noise image data, and decides a display area by using the S/N ratios and the fourth threshold.

This function differs from the image parallel display function in the second embodiment in that the details of the processing in step Sb2 in the flowchart of FIG. 7 are changed as follows. The processing in step Sb2 is changed to the processing of deciding a display area for a ultrasonic image based on ultrasonic image data and noise image data.

The arrangement described above can obtain the following effects.

The ultrasonic diagnostic apparatus 1 can decide a display area for the ultrasonic image displayed by the display unit 21 based on the image data or raw data generated by the ultrasonic image data generation unit 14, and set a specific display layout from a plurality of display layouts based on the aspect ratio of the decided display area and the number of images displayed simultaneously. This makes it possible to exclude an area in which no signal useful for diagnosis is displayed and effectively use the display screen. In addition, since the operator need not designate or adjust the display area of each ultrasonic image, operability concerning the image parallel display modes can be improved. Furthermore, it is possible to provide, for example, two image parallel display with the size of each ultrasonic image and a display layout which allow the operator to easily compare the images.

In addition, the ultrasonic diagnostic apparatus 1 can calculate an S/N ratio for each pixel of each ultrasonic image by using a noise image and decide a display area by using the calculated S/N ratios and a threshold. This makes it possible to decide a quantitative display area in consideration of noise characteristics for each ultrasonic diagnostic apparatus without any influence of noise characteristics of each ultrasonic diagnostic apparatus. As described above, therefore, the ultrasonic diagnostic apparatus 1 can decide a display range for each ultrasonic image without via the operation of the operator, and provide image parallel display optimal for the operator.

As described above, since the image parallel display mode does not require the operator to perform elaborate operations, it is possible to improve operability in the image parallel display mode and provide a display layout optimal for the operator. Furthermore, the apparatus does not reduce a plurality of images used for an image parallel display mode and does not decrease the visual field width, it is possible to display an area desired by the operator on the display screen. In addition, as the display area of each ultrasonic image, which is desired by the operator, greatly changes in accordance with the examination state, it is possible to change the display area without any instruction from the operator.

When the technical idea of the ultrasonic diagnostic apparatus 1 is to be implemented by a medical image processing apparatus 25 as a modification of the first embodiment, for example, the apparatus includes the constituent elements enclosed by the dotted line in the block diagram of FIG. 1. At this time, with regard to the processing concerning the image parallel display function, the processing of "transmitting ultrasonic waves to the object to generate ultrasonic image data" in step Sa1 in FIG. 4 in the first embodiment is changed to the processing of "reading out ultrasonic image data stored in the storage unit".

When the technical idea of the ultrasonic diagnostic apparatus 1 is to be implemented by a medical image processing apparatus 26 as a modification of the second embodiment, for example, the apparatus includes the constituent elements enclosed by the dotted line in the block diagram of FIG. 6. At this time, with regard to the processing concerning the image parallel display function, the processing of "transmitting ultrasonic waves to the object to generate ultrasonic image data" in step Sb1 in FIG. 7 in the second embodiment is changed to the processing of "reading out ultrasonic image data stored in the storage unit". In addition, the medical image processing apparatus can execute the above processing upon reading the ultrasonic image data output from the ultrasonic diagnostic apparatus.

In addition, each function according to each embodiment can be implemented by installing programs for executing the processing in a computer such as a workstation and expanding them in the memory. In this case, the programs which can cause the computer to execute the corresponding techniques can be distributed by being stored in storage media such as magnetic disks (Floppy® disks, hard disks, and the like), optical disks (CD-ROMs, DVDs, and the like), and semiconductor memories.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus comprising:
    an ultrasonic probe including a plurality of transducers configured to perform ultrasonic scans, the ultrasonic probe being connected to a main body;
    a display attached to the main body; and
    processing circuitry configured to
        preset diagnostic parameters before performing the ultrasonic scans, diagnostic parameters including a visual field depth and an azimuth angle,
        generate a plurality of ultrasonic images based on outputs from the ultrasonic probe as a result of the ultrasonic scans,
        set a first display layout or a second display layout selectively based on the visual field depth and the azimuth angle of the plurality of ultrasonic images, the first display layout being a layout laterally parallelly displaying the plurality of ultrasonic images and the second display layout being a layout vertically parallelly displaying the plurality of ultrasonic images, and
        cause the display to display the plurality of ultrasonic images in accordance with the preset diagnostic parameters and the set display layout, the processing circuitry being contained in the main body, wherein the processing circuitry is configured to
        automatically set the first display layout or the second display layout selectively in response to an input by a user to perform a switching operation to switch a number of ultrasonic images to be displayed on the display from one to a plural number, and
        when an enlarged display instruction is input to enlarge, from a first magnification, part of one ultrasonic image of the plurality of ultrasonic images while the plurality of ultrasonic images are being displayed in accordance with the set display layout, and when an aspect ratio of a display area of the enlarged part of the one ultrasonic image exceeds a predetermined threshold, set the other layout that was not previously set, and display on the display the part of the one ultrasonic image and parts of other ultrasonic images corresponding to the part of the one ultrasonic image that are all enlarged at a same magnification that is greater than the first magnification.

2. The apparatus of claim 1, wherein the processing circuitry is configured to set the first display layout or the second display layout based on azimuth angles or image widths of the plurality of ultrasonic images, the visual field depths of the plurality of ultrasonic images, and a number of ultrasonic images for simultaneous display, the number being input together with the input to perform the switching operation.

3. The apparatus of claim 1, wherein the processing circuitry is configured to, when the plurality of ultrasonic images are displayed in accordance with the first display layout, set the second display layout in response to setting or inputting of a transmission frequency higher than a frequency threshold, the transmission frequency being used for transmission to an object.

4. The apparatus of claim 1, wherein the plurality of ultrasonic images include an image updated in real time.

5. The apparatus of claim 1, wherein the plurality of ultrasonic images include an image at a time of a freezing operation.

6. The apparatus of claim 1, wherein the plurality of ultrasonic images include images generated by different modes.

7. The apparatus of claim 4, wherein the plurality of ultrasonic images include images generated by different modes.

8. The apparatus of claim 1, wherein the plurality of ultrasonic images include images generated by a B-mode.

9. The apparatus of claim 1, wherein the plurality of ultrasonic images includes two ultrasonic images.

10. The apparatus of claim 1, wherein the processing circuitry is configured to display on the display the part of the one ultrasonic image and the parts of other ultrasonic images corresponding to the part of the one ultrasonic image that are all enlarged at the same magnification that is greater than the first magnification, such that parts that have a same position in the image are enlarged at a same rate.

11. A medical image parallel display method comprising:
    presetting diagnostic parameters before performing ultrasonic scans, diagnostic parameters including a visual field depth and an azimuth angle;
    performing the ultrasonic scans by an ultrasonic probe based on the diagnostic parameters;
    generating a plurality of ultrasonic images based on outputs from the ultrasonic probe as a result of the ultrasonic scans;
    setting, using processing circuitry, a first display layout or a second display layout selectively based on the visual field depth and the azimuth angle of the plurality of ultrasonic images, the first display layout being a layout laterally parallelly displaying the plurality of ultrasonic images and the second display layout being a layout vertically parallelly displaying the plurality of ultrasonic images; and displaying, on a display, the plurality of ultrasonic images in accordance with the preset diagnostic parameters and the set display layout, wherein the setting automatically sets the first display layout or the second display layout selectively in response to an input by a user to perform a switching operation to switch a number of ultrasonic images to be displayed on the display from one to a plural number, and when an enlarged display instruction is input to enlarge, from a first magnification, part of one ultrasonic image of the plurality of ultrasonic images while the plurality of ultrasonic images are being displayed in accordance with the set display layout, and when an aspect ratio of a display area of the enlarged part of the one ultrasonic image exceeds a predetermined threshold, the other layout that was not previously set is set, and the part of the one ultrasonic image and parts of other ultrasonic images corresponding to the part of the one ultrasonic image that are all enlarged at a same magnification that is greater than the first magnification are displayed on the display.

12. The medical image parallel display method of claim 11, wherein the plurality of ultrasonic images includes two ultrasonic images.

13. An ultrasonic diagnostic apparatus comprising:
an ultrasonic probe including a plurality of transducers configured to perform ultrasonic scans, the ultrasonic probe being connected to a main body;
a display attached to the main body; and
processing circuitry configured to
generate a plurality of ultrasonic images based on outputs from the ultrasonic probe as a result of the ultrasonic scans,
set a first display layout or a second display layout selectively based on an aspect ratio of a display area of the ultrasonic image, the first display layout being a layout laterally parallelly displaying the plurality of ultrasonic images and the second display layout being a layout vertically parallelly displaying the plurality of ultrasonic images, and
cause the display to display the plurality of ultrasonic images in accordance with the set display layout, the processing circuitry being contained in the main body, wherein the processing circuitry is configured to
automatically set the first display layout or the second display layout selectively in response to an input by a user to perform a switching operation to switch a number of ultrasonic images to be displayed on the display from one to a plural number, and
when an enlarged display instruction is input to enlarge, from a first magnification, part of one ultrasonic image of the plurality of ultrasonic images while the plurality of ultrasonic images are being displayed in accordance with the set display layout, and when an aspect ratio of a display area of the enlarged part of the one ultrasonic image exceeds a predetermined threshold, set the other layout that was not previously set, and display on the display the part of the one ultrasonic image and parts of other ultrasonic images corresponding to the part of the one ultrasonic image that are all enlarged at a same magnification that is greater than the first magnification.

14. The apparatus of claim 13, wherein
the plurality of ultrasonic images include an image updated in real time, and
the processing circuitry is configured to, when the plurality of ultrasonic images are displayed in accordance with the first display layout, set the second display layout in response to setting or inputting of a transmission frequency higher than a frequency threshold, the transmission frequency being used for transmission to an object.

15. The apparatus of claim 13, wherein the plurality of ultrasonic images includes two ultrasonic images.

* * * * *